United States Patent [19]

Forney et al.

[11] Patent Number: 5,209,904
[45] Date of Patent: May 11, 1993

[54] AGGLUTINATION REACTION DEVICE UTILIZING SELECTIVELY IMPREGNATED POROUS MATERIAL

[75] Inventors: Kevin J. Forney, Chicago; Robert G. Parsons, Green Oaks, both of Ill.; Paul J. Ropella, Racine, Wis.; Bob O. Basore, Evanston; Michael B. O'Connell, Waukegan, both of Ill.

[73] Assignee: Abbott Laboratories, Abbott Park, Ill.

[21] Appl. No.: 614,762

[22] Filed: Nov. 16, 1990

Related U.S. Application Data

[63] Continuation-in-part of Ser. No. 138,253, Dec. 23, 1987, abandoned.

[51] Int. Cl.⁵ .......................................... G01N 21/03
[52] U.S. Cl. .................................. 422/73; 422/58; 422/61; 422/101; 422/102; 436/46; 436/165; 436/177; 436/178; 356/244; 359/396; 359/398
[58] Field of Search ............... 422/73, 58, 61, 101, 422/102; 436/46, 165, 177, 178, 63, 69; 356/244, 246; 350/534, 536

[56] References Cited

U.S. PATENT DOCUMENTS

| | | | |
|---|---|---|---|
| 4,426,451 | 1/1984 | Columbus | 436/165 X |
| 4,557,600 | 12/1985 | Klose et al. | 436/45 X |
| 4,596,695 | 6/1986 | Cottingham | 422/102 X |
| 4,654,197 | 3/1987 | Lilja et al. | 422/56 |
| 4,761,381 | 8/1988 | Blatt et al. | 422/102 X |
| 4,775,515 | 10/1988 | Cottingham | 422/102 X |
| 4,849,340 | 7/1989 | Oberhardt | 422/110 X |
| 4,857,453 | 8/1989 | Ullman et al. | 422/58 X |
| 4,906,439 | 3/1990 | Grenner | 422/56 |
| 4,963,498 | 10/1990 | Hillman et al. | 422/73 X |
| 5,019,351 | 5/1991 | Schulz | 422/73 X |

FOREIGN PATENT DOCUMENTS

0321736  6/1989  European Pat. Off. .

Primary Examiner—Lynn M. Kummert
Attorney, Agent, or Firm—Thomas M. Breininger

[57] ABSTRACT

An improved device for performing agglutination reactions is disclosed. The device has at least one chamber with a proximate zone and a distal zone in which chamber agglutination reactions can be performed. The improvement comprises utilization in the device of a layer of liquid absorbent material for controlling overall rate of liquid flow through the chamber. The layer of liquid absorbent material is selectively impregnated with a substance to form an impregnated region and a non-impregnated region wherein the non-impregnated region is liquid absorbent and the impregnated region is liquid-occlusive. A portion of the non-impregnated region is positioned within the distal zone of the chamber so that the non-impregnated region is in liquid communication with that zone.

20 Claims, 4 Drawing Sheets

AGGLUTINATION REACTION DEVICE UTILIZING SELECTIVELY IMPREGNATED POROUS MATERIAL

This application is a continuation-in-part of copending application Ser. No. 07/138,253, filed on Dec. 23, 1987, entitled "Agglutination Reaction Device", now abandoned, the disclosure which is incorporated herein by reference.

BACKGROUND OF THE INVENTION

The present invention is directed to a device for performing an agglutination reaction of immunochemical particles. The agglutination reaction device is designed to provide a convenient means for performing and reading the results of an agglutination reaction.

Agglutination reactions and their procedures are generally well known in the art. A typical agglutination reaction consists of the clumping together (or aggregation) in suspension of antigen- or antibody-bearing cells, microorganisms, or particles in the presence of specific analytes. This clumping or agglutination of particles is then monitored to determine the absence or presence of an analyte sought to be detected.

One method for reacting immunochemical particle reagents is to place liquid reagents on a glass slide and generally rock or swirl the slide back and forth to cause the reagents to mix and form agglutinations. Methods have also been developed to avoid the necessary swirling of the particle reagents in order to visualize the agglutinations. For example, U.S. Pat. No. 4,596,695 discloses an agglutination reaction chamber for reacting immunochemical particle reagents. The chamber includes a first transparent panel having a first surface and a second panel having a second surface spaced apart from the first surface to define a chamber between. The chamber intrinsically causes immunochemical particle reagents to flow by capillary action without an external motion imparted to the chamber during which flow the immunochemical particle reagents can react.

An object of the present invention is to provide a device that can be easily adapted for use in the automated diagnosis of a plurality of samples. Another object of the present invention is to provide a device capable of performing multiple, highly sensitive, diagnostic tests simultaneously on a single sample in a single device. In particular, the present invention is directed toward a device that can be used in an automated fashion where the reaction can be rapidly performed and monitored with a minimum of sample material. In another aspect, the present invention is directed to a device having multiple channels radiating from a central well where multiple reactions on a single sample can be rapidly performed and monitored with a minimum of sample material with the results of such reactions being easily, visibly observable. In particular, the present invention is directed to an improved device for performing agglutination reactions which device has means for controlling the overall rate of liquid flow through the device comprising a porous absorbent material in liquid communication with a capillary chamber in the device. material in liquid communication with a capillary chamber in the device.

SUMMARY OF THE INVENTION

The present invention is directed to a device having an agglutination reaction chamber for performing agglutination immunoassay reactions. In one aspect, the invention is directed to an improved device for performing agglutination reactions having at least one chamber having a proximate zone and a distal zone, in which chamber agglutination reactions can be performed. The improvement comprises utilization in the device of means for controlling overall rate of liquid flow through the chamber, the means comprising a layer of liquid absorbent material selectively impregnated, preferably through its thickness, with a substance to form an impregnated region and a non-impregnated region wherein the non-impregnated region is liquid absorbent and the impregnated region is liquid-occlusive. The non-impregnated region is in liquid communication with the distal zone of the chamber.

The present invention also provides a device for performing agglutination reactions comprising: in adherent relationship, a first wettable layer, a second layer parallel to and overlying the first layer, and a third layer parallel to and overlying the second layer and having a window for observing agglutinated particles. The second layer is interposed between, and is in adherent relationship to, the first and third layers. The second layer comprises a liquid absorbent material selectively impregnated, preferably through its thickness, with a substance to form an impregnated region and a non-impregnated region. The non-impregnated region is liquid absorbent and the impregnated region is liquid-occlusive. The second layer has a slot in the impregnated region defining a channel for directing liquid conducted by capillary action through a chamber defined by the slot in conjunction with the first and third layers. Agglutination reactions can be performed in the chamber. The chamber has a proximate zone and a distal zone and means for controlling the overall rate of liquid flow through the chamber. The means for controlling the overall rate of liquid flow through the chamber comprises the non-impregnated region of the second layer which non-impregnated region is in liquid communication with the chamber and is located adjacent to the distal end of the chamber.

Additionally, the present invention provides for a device for performing simultaneously a plurality of agglutination reactions. The device comprises, in adherent relationship, a first wettable layer, a second layer parallel to and overlying the first layer, and a third layer parallel to and overlying the second layer and having windows for observing agglutinated particles. The second layer is interposed between and is in adherent relationship to the first and third layers. The second layer comprises a liquid absorbent material selectively impregnated, preferably through its thickness, with a substance to form an impregnated region and a plurality of non-impregnated regions. The non-impregnated regions are liquid absorbent and the impregnated regions are liquid-occlusive. The second layer has a plurality of slots in radial spatial relationship to each other in the impregnated region. These slots in radial spatial relationship to each other define channels for directing liquid conducted by capillary action through chambers defined by the slots in conjunction with the first and third layers. Within these chambers, agglutination reactions can be performed simultaneously. Each of the chambers has a proximate zone and a distal zone and means for controlling the overall rate of liquid flow through the chamber, which means comprises a non-impregnated region of the second layer which non-impregnated region is in liquid communication with the chamber and is located adjacent to the distal end of the chamber. For example, the annular ring (27) in FIG. 3 bonded to layer (2) provides the second layer (2) with respective impregnated liquid-occlusive regions (26) and non-impregnated liquid absorbent regions (4).

In an agglutination reaction chamber of the present invention the reagent can be present in dried spots or strips. It is also possible to suspend the reagent in a water-soluble polymer.

A copending United States patent application, Ser. No. 07/138,253, filed on Dec. 23, 1987, now abandoned, entitled "Agglutination Reaction Device" (the disclosure of which is hereby specifically incorporated herein by reference), teaches an agglutination reaction chamber which is constructed to be very small in size to accommodate automated and efficient use of sample and reagents. Typically, the length of such a chamber is from about 10 to about 75 millimeters (mm), the channels are from about 0.01 to about 5.0 mm in depth and from about 0.1 to about 10.0 mm in width. A typical overall size for such an agglutination reaction device having four chambers and a sample receiving well is about 37.5 mm $\times$ 12.5 mm $\times$ 1.5 mm (l $\times$ w $\times$ h).

The aforesaid copending United States patent application also generally discloses a means for controlling the flow of fluid in an agglutination reaction chamber involving the configuration of the channel or geometric formations within the channel such as ridges, particularly ridges formed in the channel which extend across the entire width of the channel and for at least a portion of the length of the channel. The aforesaid copending United States patent application also discloses another means for controlling the flow of fluid in the chamber, namely utilization of a water-soluble material, such as a water-soluble polymer, (e.g., polyvinylpyrrolidone, polyvinylalcohol, gelatin, or bovine serum albumin) dried in portions of the channel.

However, it has been found that such expedients, while useful in helping to control the overall rate of liquid (fluid) flow in the channels, can be difficult to employ so as to obtain consistently uniform results. For example, where a water-soluble polymer such as polyvinlypyrrolidone is utilized, it has been found that it can be difficult to obtain dried coatings of the polyvinylpyrrolidone so as to obtain consistent stability of overall flow of liquid in the channels. Also, there are advantages with respect to the ease of manufacture of devices utilizing a porous absorbent medium such as paper compared to utilization of coatings such as dried polyvinylpyrrolidone.

The present invention is directed to devices for performing agglutination reactions having improved properties including improved means for controlling the overall rate of liquid flow through the agglutination chamber. The present invention also is directed to such devices constructed in the form of convenient, disposable structures, such as disposable, laminated cards, optionally mounted in disposable rigid containers.

A copending United States patent application entitled, "Improved Agglutination Reaction Device Utilizing A Porous Absorbent Material, filed even date herewith, is directed to devices for performing agglutination reactions having improved properties including improved means for controlling the overall rate of liquid flow through an agglutination chamber.

DETAILED DESCRIPTION OF THE PREFERRED EMBODIMENTS

The present invention is directed toward improved devices suitable for performing agglutination reactions. Two embodiments of the invention are shown in FIGS. 1 and 2.

Figure 1:
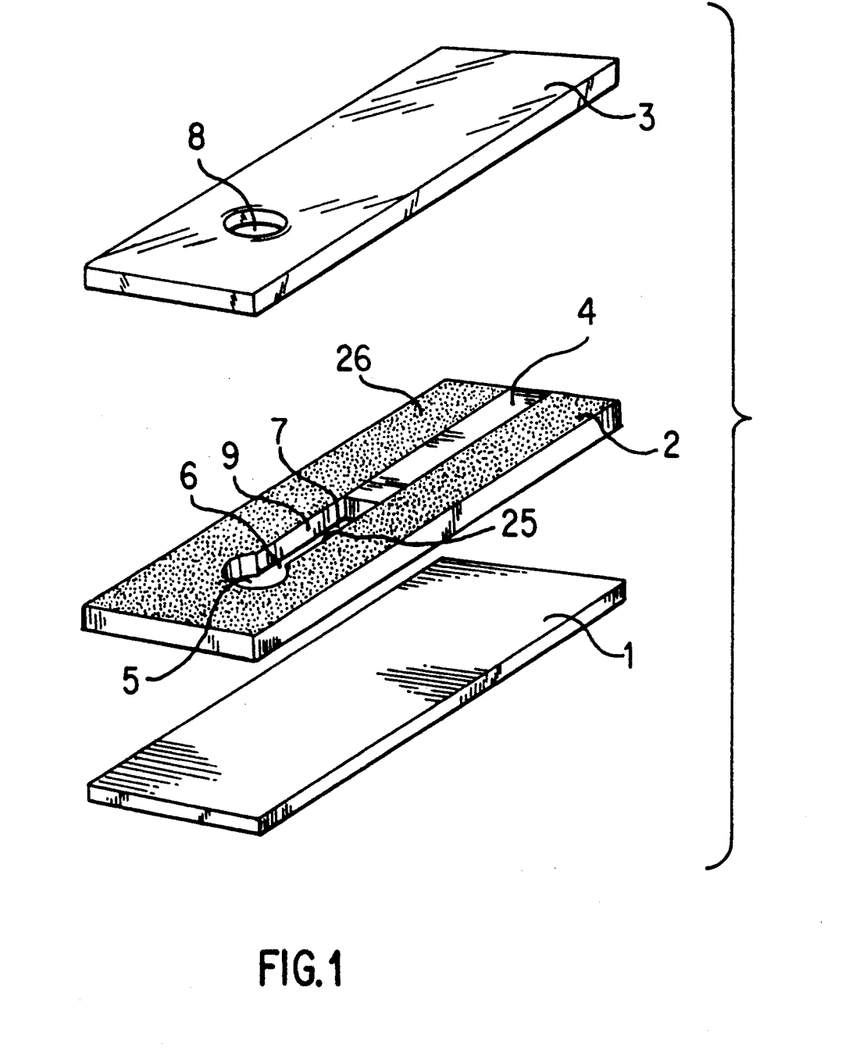
FIG. 1 is an exploded, top perspective view of an embodiment showing a three layer structure comprising a first or base layer, a second layer showing a cutout for a round receiving well and a generally straight agglutination chamber with an integral porous absorbent strip in the second layer at the distal end, and a third or top layer.
Figure 2:
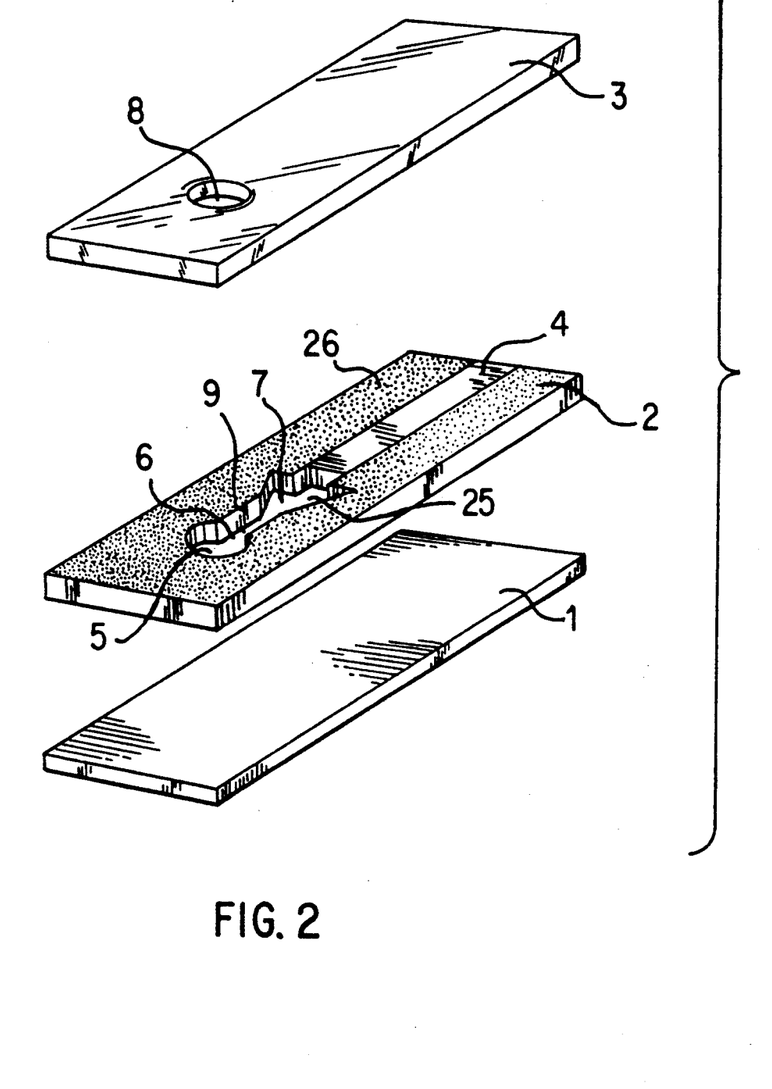
FIG. 2 is an exploded, top perspective view of another embodiment showing a three layer structure comprising a first or base layer, a second layer showing a cutout for a round receiving well and an agglutination chamber having a flared portion at its distal end with an integral porous absorbent strip in the second layer at the distal end of the chamber, and a third or top layer.

FIGS. 1 and 2 illustrate embodiments of a device for performing agglutination reactions, in the form of a laminated card when the layers shown in FIGS. 1 and 2 are adhered or laminated together. These embodiments have, in adherent relationship, a first wettable, but liquid-occlusive, layer (1), a second layer (2) parallel to and overlying the first layer (1), and a third liquid-occlusive, preferably non-wettable, layer (3) parallel to and overlying the second layer (2) and having a window, or viewing area, for observing particles. The first layer (1) is made of a liquid-occlusive material having a water-wettable surface. In this embodiment the third layer (3) is made from a clear, liquid-occlusive, preferably non-wettable, film, such as a clear polycarbonate film or a non-wettable cellophane tape, and therefore also serves as a window, or viewing area, for observing particles in the agglutination chamber. The second layer (2) is interposed between, and is adhered to, the first layer (1) and third layer (3), for example by means of an adhesive on each side of layer (2) facing the top-side of the first layer (1) and the underside of the third layer (3) respectively. The second layer (2) has a slot (25) cut through its thickness defining a channel for directing liquid for conduction by capillary action through the chamber defined by the slot (25) in conjunction with the first (1) and third (3) layers respectively.

In other words, when the first, second and third layers are laminated together a portion of each of the first and third layers serve respectively as the floor and roof of the agglutination chamber with part of the walls of the slot (25) of the second layer (2) defining the walls (9) of the chamber, the other part of the walls of slot (25) defining the walls of the circular receiving well (5) The agglutination reaction chamber has a proximate zone (6) and a distal zone (7), which proximate zone (6) for example in FIG. 2 is represented by the generally rectangular portion of the slot (25) of the second layer (2) with the distal zone (7) being represented by the deltoid or flared portion of the slot (25) of the second layer (2).

In the embodiments of FIGS. 1 and 2, the second layer (2) is made of a liquid absorbent material, such as absorbent paper, selectively impregnated through its thickness with a substance, such as a water-repellent ink, to form an impregnated region (26) and a non-impregnated region (4). The non-impregnated region (4) is liquid absorbent and the impregnated region (26) is liquid-occlusive. In these embodiments, the non-impregnated region (4) which is in liquid communication with the distal zone (7) of the chamber serves as the means for controlling the overall rate of liquid flow through the agglutination chamber. The second layer (2) also has a slot (25) in the impregnated region (26) defining a channel for directing liquid conducted by capillary action through a chamber defined by the slot (25) in conjunction with the first layer (1) and third layer (3). This chamber also has a proximate zone (6) and a distal zone (7). It is within this chamber that agglutination reactions can be performed. As can be seen from FIGS. 1 and 2, the non-impregnated region (4) is located adjacent to the distal end of the agglutination chamber and is in liquid communication with the chamber.

Also in the embodiments illustrated by FIGS. 1 and 2 there is a well-defining slot (8) in the third layer (3) and a corresponding second well-defining slot (5) in the second layer (2) of the same size and configuration as the well-defining slot (8) in the third layer (3) The well-defining slot (5) in the second layer (2) is positioned directly below the well-defining slot (8) in the third layer (3) such that when all three layers are laminated together, the second well-defining slot (5) in conjunction with the well-defining slot (8) along with the corresponding portion of the first layer (1) define a circular well for receiving liquid, the well being in liquid communication with the proximate zone (6) of the chamber. The bottom of the well is formed from a corresponding circular portion of the first layer (1) which portion can be considered to be the projection of the outline of slots (5) and (8) onto the surface of layer (1).

When, for example, a solution of cells is introduced into the receiving well of a device of the invention, which well is in liquid communication with the proximate end of the reaction chamber; and the chamber contains antibodies directed against antigens on the cells and which antigens are dried onto the floor of the chamber, the solution will migrate through the chamber by capillary action, mix with the antisera, and the cells will aggregate. This will all occur without any centrifugation or mixing steps. Control of the overall rate of flow of the liquid through the channel is necessary because the agglutination reaction occurs preferably during the period of liquid flow. Sufficient incubation time is built into the period of liquid flow to achieve optimum reaction of the reagents.

Figure 3:
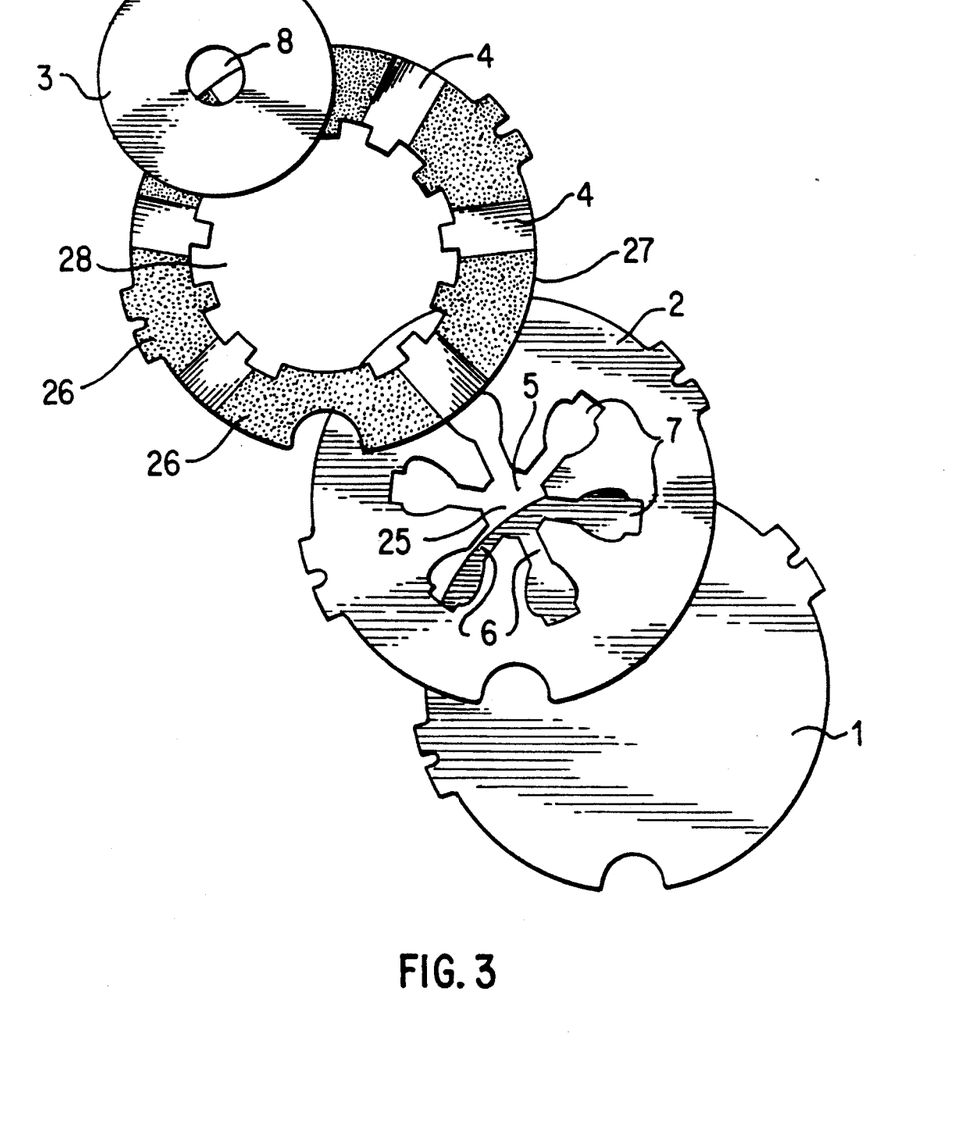
FIG. 3 is a top plan view of another embodiment showing the parts of a laminated structure comprising a base layer, a second layer having a cutout for a round receiving well and multiple radiating agglutination chambers having flared distal zones, an annular structure (ring) for the second layer having alternating liquid absorbent regions (4) and liquid-occlusive regions (26), and another round layer which in cooperation with the annular structure forms the top layer.

FIG. 3 illustrates an exploded, plan view of a preferred embodiment of the invention. This embodiment provides for performing a plurality of agglutination reactions utilizing a minimal amount of liquid sample. The device in assembled form can be thought of a relatively thin, laminated, disposable structure having in this particular illustration six agglutination chambers radiating from a common liquid receiving well. The device of FIG. 3 comprises, in adherent relationship, an approximately circular first wettable but liquid-occlusive layer (1), an approximately circular second liquid-occlusive layer (2) parallel to and overlying the first layer (1), and a third liquid-occlusive layer (3) parallel to and overlying the second layer (2) These respective layers can be bonded together, for example, by means of an adhesive between the respective layers. In this embodiment the third layer (3) is made of a circular clear plastic film, such as a polycarbonate film, thereby providing windows, or viewing areas, for observing particles in the six radiating agglutination chambers. The second layer (2), interposed between and in adherent relationship to the first and third layers has a slot (25) in the form of a central, circular portion (5) having six radial, slotted arms extending outward therefrom. These radial arms of the slot (25) define six channels for directing liquid conducted by capillary action through chambers respectively defined by the radial, slotted arms in conjunction with the first layer (1) and the third layer (3). Within the resulting six chambers agglutination reactions can be performed simultaneously. Each of the six chambers has a generally rectangular proximate zone (6) and a generally flared or deltoid shaped distal zone (7). The overall rate of liquid flow through each agglutination chamber in this embodiment is controlled by means of a strip of porous absorbent material (4), preferably filter paper, projecting from a generally annular ring (27) of such porous material having a hole (28), into the distal zone (7) of each of the channels defined by the radial, slotted arms. The annular ring (27) in the completed, laminated assembly, is to be considered part of layer (2) for the purposes of the invention. The annular ring (27) is selectively impregnated through its thickness with a substance to provide alternating non-impregnated liquid absorbent regions (4) and impregnated liquid-occlusive regions (26). These non-impregnated strips (4) of paper projecting from the annular ring (27) are in liquid communication with the chambers and are positioned adjacent to the distal ends of the chambers, preferably positioned partially in the distal ends, when the structures of FIG. 3 are laminated respectively together.

The third layer (3) of the device represented by FIG. 3 has a circular well-defining slot (8), and the second layer has a corresponding circular second well-defining slot (5) of the same size and configuration as the well-defining slot (8) in the third layer (3). The well-defining slot (5) of the second layer (2) is positioned directly below the well-defining slot in the third layer (3) in the assembled configuration. Thus the second well-defining slot (5) in conjunction with the well-defining slot (8) in the third layer (3) and the respective circular portion of the first layer (1) define a well for receiving liquid, the well being in liquid communication with the proximate zone (6) of each of the chambers.

The resulting, generally circular laminated structure, can be thought of as being in the form of a relatively thin, disposable card with the fluid-absorbent paper strip (4) being in liquid communication with the distal zone (7) of the agglutination chamber. Thus, in all of the embodiments of the present invention, the device of the invention has means for controlling overall rate of liquid flow through the reaction chamber which is a porous absorbent material in liquid communication with the chamber, which material is typically positioned adjacent to, and usually extending partially into, the distal end of the chamber. The aforesaid porous material, for example paper, is to be distinguished from water-soluble materials such as dried coatings of water-soluble polymers such as polyvinylpyrrolidone, polyvinylalcohol, gelatin, or bovine serum albumin. The porous absorbent material utilized in present invention is itself generally not water-soluble.

Figure 4:
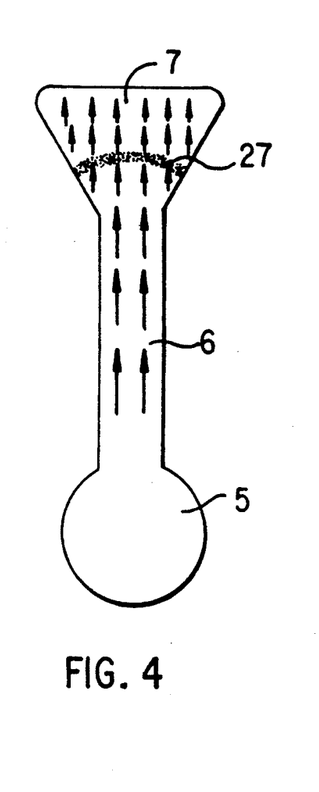
FIG. 4 is a schematic diagram illustrating regions of different flow rate per unit area outward from the receiving well for an agglutination chamber having a flared distal end, and illustrating a band of agglutinated particles in the flared distal end.

It has been found that the utility of devices of the present invention, for performing agglutination reactions, can be enhanced further by utilizing an additional means for controlling the flow of liquid through the reaction chamber of the device, by modifying the geometric configuration of the chamber or the internal shape of the chamber as illustrated in FIGS. 2, 3 and 4. For example, in FIGS. 2 and 3, the general slot (25) in layer (2) defines at least approximately parallel walls (9) in the proximate zone (6) of the chamber thereby defining a first path of approximately constant width. Looking in the direction toward the distal end of the chamber, the general slot (25) defines walls in the distal zone (7) which are spaced to define a second path of increased width compared to the first path of the proximate zone (6). It has been found that agglutination reactions performed in such a chamber advantageously can result, surprisingly, in the formation of one or more patterned formations, such as, for example bands, of agglutinated particles in the distal zone (7) of the chamber which patterns are more easily observable through the window of the third layer (3) than non-patterned aggregates of agglutinated particles which generally result in agglutination chambers of the prior art. FIG. 4 shows a schematic representation of an approximately semicircular band (27) of agglutinated particles in the zone of increasing chamber width, namely in the flared (were approximately deltoid-shaped) "second path" of the chamber in the distal zone (7) of the chamber. As represented in schematic form in FIG. 4 through the use of arrows of different length along the reaction path in the chamber, the walls in the distal zone (7) are spaced to provide a decreased liquid flow rate per unit area of liquid path along this second path. In FIG. 4, the shorter arrows are, of course, intended to represent smaller flow rate per unit area of path, compared to that represented by the longer arrows.

Figure 5:
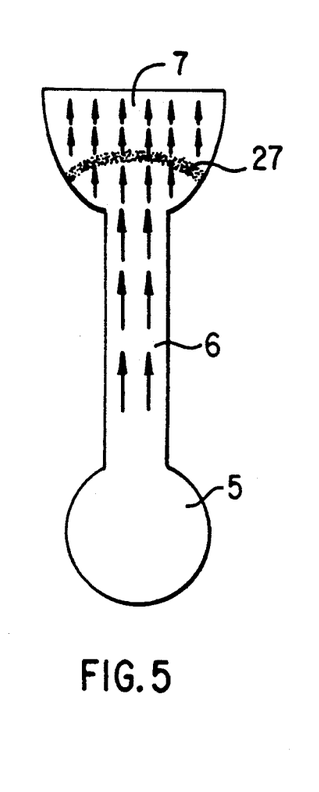
FIG. 5 is a schematic diagram illustrating regions of different flow rate per unit area outward from the receiving well for an agglutination chamber having semicircular, or bowl-shaped, distal end, and illustrating a band of agglutinated particles in the semicircular end.
Figure 6:
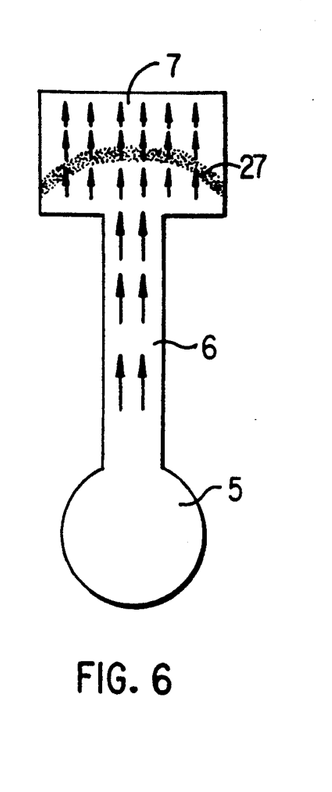
FIG. 6 is a schematic diagram illustrating regions of different flow rate per unit area outward from the receiving well for an agglutination chamber having an approximately rectangular shape, and illustrating a band of agglutinated particles in the rectangular area of increased width.

While deltoid-shaped configurations of the second path of the distal zone in the chambers is preferred, it has been found that other geometric configurations for this so-called "second path" provide advantageous patterned formations of agglutinated particles. For example, the side walls in the second path can be formed to be convex giving an approximately semicircular or bowl-shaped configuration to the second path as illustrated in FIG. 5. Alternatively, although less preferred, the side walls of the second path can be formed to provide the second path with an approximately rectangular shape as illustrated in FIG. 6.

Moreover, if desired, the flow rate per unit area in the distal zone of the reaction chamber can be gradually decreased along the general direction of flow by gradually increasing the space between the floor and the roof of the chamber along the direction of liquid flow, for example by gradually bowing the roof of the chamber in the distal zone upward and/or gradually bowing the floor of the chamber in the distal zone downward. It has been found that such modification of the space between the floor and the roof of the chamber in the distal zone of the chamber can also contribute to the formation of regular patterns of agglutinated particles being formed in the distal zone of the chamber. For example, the space between the floor and the roof of the chamber can be gradually increased by stamping a spherical dome-shaped or cylindrical dome-shaped configuration in an area of the third layer (3) in such manner that when the third layer is adhered to the second layer (2) the dome in the third layer overlies the distal zone of the reaction chamber. Another example of a way to provide a gradually increasing space between the floor and the roof of the distal zone of the reaction chamber is to stamp a spherical bowl-shaped or cylindrical bowl-shaped depression in the base or first layer (1) in such manner that when the first layer (1) is adhered to the second layer (2) the bowl-shaped depression occurs in the floor of the distal zone of the reaction chamber.

All types of agglutination-based assays can be accommodated with a device according to the present invention. In some instances, a soluble reagent can be dried as spots or strips in the reaction chamber, for example, in blood typing. In other instances, a particulate reagent, such as a latex reagent, can be dried in the chamber. In yet another approach, a reagent can be dispersed in a solution which is placed in the chamber. One preferred reagent solution is microparticulates in a solution of dextran and sucrose. Preferably, the microparticulate reagent is mixed in a solution of about 2.5 to about 5.0 percent by weight dextran and from about 15 to about 20 percent by weight sucrose. Another preferred solution for mixing reagents is FICOLL (a trademark by Sigma Chemical Co., St. Louis, Mo. for a nonionic synthetic polymer of sucrose) from about 20 to about 30 percent by weight. Also, depending on the requirements of the assay, the flow of the liquid through the chamber can be controlled as described above to accommodate any necessary incubation times and assay sequences.

A particularly advantageous feature of the present invention is that it provides for the ability to simultaneously perform multiple assays while utilizing a very small amount of sample material, for instance, a single drop. Also, the agglutination assay is essentially self-performing once the drop has been added to the agglutination reaction device. Moreover, in those embodiments of the invention utilizing an additional means for controlling the flow of liquid through the reaction chamber of the device, namely by modification of the geometric configuration of the chamber or the internal shape of the chamber as discussed above, additional enhanced results can be obtained such as enhanced observability of aggregates of agglutinated particles in the distal zone of the reaction chamber.

A device of the invention is suitable for use in an automated fashion where the agglutination reaction can be monitored by an optical scanner. For example, the construction of the agglutination reaction device enables one to use an image analysis system available from Olympus (CUE-2, Lake Success, N.Y.) to determine the quantity and concentration of agglutinated material. The agglutination reaction device is illuminated, such that transmitted or reflected light can be read by the reader. The image is then computer analyzed to determine the quantity of agglutination which has occurred and to enhance the image for very accurate and sensitive determinations. By confining the sample to a chamber such as formed in the agglutination reaction device, there is no problem with curvatures of droplets or water which could interfere with the image seen by the reader. Thus, the uniformity of the reacted sample and reagents achieved by the agglutination reaction device provides an excellent imaging format for a reader or other imaging devices. Besides being able to read the transmission of light through the bottom of the agglutination reaction device, it is also possible to read reflected light because the sample and reacted reagents are confined to capillary chambers formed by the agglutination reaction device.

It is required that a surface, preferably the bottom surface, of an agglutination chamber of the present invention be hydrophilic or wettable such that capillary flow is induced when a sample is placed in contact with the ingress of the proximate zone of the chamber. This can be accomplished by using a hydrophilic or water-wettable material for the surface. However, it is also possible to chemically treat or coat otherwise non-wettable (hydrophobic) materials such that they become wettable. This preparation of a wettable surface can also be used to influence the flow rate in the capillary chamber.

Suitable materials for preparing a wettable layer for various embodiments of the invention include, for example, cellulose acetate butyrate, a wettable nylon material, or a layer coated with an acrylic latex emulsion to render the surface water-wettable. The "roof" of an agglutination chamber of the invention may be either wettable or non-wettable.

The small size of the reaction devices of the invention allows for the rapid and convenient handling of a plurality of devices and therefore samples. A device can then be loaded into an automated apparatus which indexes and scans the individual channels for the assay result and records this information for future access. The small dimensions of the agglutination reaction device also provide for efficient use of sample and reagents.

The following examples are provided to further illustrate embodiments of the invention and should not be construed as a limitation on the scope of the invention.

EXAMPLE 1

A 3 inch square pad of Whatman No. 1 filter paper was screen printed on both sides with a heat cured vinyl resin (6C-33 Resin from Olin-Hunt, Ontario, Calif.). The printed pattern contained non-saturated (i.e., non-impregnated) areas (regions) that were shaped like area (4) in FIG. 3. The parts were then laminated on both sides with transfer adhesive. After die cutting the shape (slot (25) in FIG. 1) of the chamber in the sandwich as shown in FIG. 1, the layer was laminated between a wettable coated base layer (layer 1) and a clear polycarbonate top layer (layer 3) to form a capillary track (i.e., an agglutination chamber). SeraSub TM (a synthetic serum from Creative Scientific Technology, Inc., Great Neck, N.Y.) was added to the sample well and flowed up the capillary track to the strip-shaped non-impregnated (unprinted) area (region) of filter paper where it slowly absorbed until the non-impregnated area became saturated. Such a printed pattern eliminated the need for separate strips of absorbent material.

EXAMPLE 2

Twenty-five microliters of a 10% (volume/volume) suspension of Type A human red blood cells are mixed with 25 microliters of commercial anti-A blood-typing antisera and introduced into the well (5) of FIG. 1 of the device from Example 1. The liquid rapidly fills the capillary channel through distal zone (7) and then slowly saturates the non-impregnated paper region (4). Agglutinated clusters of cells form in the distal zone (7) of the capillary reaction chamber.

EXAMPLE 3

Laminated disposable cards were prepared by assembling together a wettable base layer, a die-cut adhesive core layer, an impregnated filter paper ring, and a clear polycarbonate top layer as shown in FIG. 3. The wettable base layer consisted of a die-cut piece of paperboard coated with an acrylic latex emulsion (Daubert Coated Products, Dixon, Ill.). Channel shapes were die-cut in a 3.1 mil double-coated adhesive film (ARCare 7580, Adhesive Research, Glen Rock, Pa.) to form the adhesive core layer. The impregnated filter paper ring utilized a hot melt adhesive applied with a rotary screen process to establish the non-impregnated strip-shaped areas. The material used was a 4.0 mil cellulosic paper (Grade 86150, Fletcher Paper Co., Alpena, Mich.). Prior to die-cutting the ring shape, the impregnated paper was laminated to a single-side adhesive coated polyester film (ARCare 7597, Adhesive Research, Glen Rock, Pa.) which served to minimize evaporative losses. Finally, a die-cut donut-shaped piece of clear polycarbonate film (GE Part 8040-112, Cadillac Plastics, Evansville, Ind.) was laminated onto the base/core/impregnated paper subassembly using a mechanical laminator set at 50 pounds per square inch (psi) and 0.2 feet per second (ft/sec).

EXAMPLE 4

A three-inch square pad of Whatman No. 1 filter paper was screen printed on both sides with a heat cured vinyl resin. The printed pattern contained nonsaturated areas that were shaped like the paper strip assemblies in Example 1. The parts were then laminated on both sides with transfer adhesive. After die-cutting the shape of the track in the sandwich as shown in FIG. 2, the layer was laminated between a wettable coated base layer and a clear polycarbonate top layer to form a capillary track. SeraSub was added to the sample well and flowed up the track to the strip-shaped unprinted filter paper section, where it was slowly absorbed until saturation. The pattern coating eliminated the need for separate strips.

We claim:

1. A device for performing agglutination reactions comprising: in adherent relationship, a first hydrophilic layer, a second layer parallel to and overlying said first layer, and a third layer parallel to and overlying said second layer and having a window for observing agglutinated particles, said second layer interposed between and in adherent relationship to said first and third layers, said second layer comprising a liquid-absorbent material selectively impregnated with a substance to form an impregnated region and a non-impregnated region wherein said non-impregnated region is liquid-absorbent and said impregnated region is liquid-occlusive, said second layer including means defining a slot in said impregnated region and defining a channel for directing liquid conducted by capillary action through a chamber defined by said slot in conjunction with said first and third layers and within which chamber agglutination reactions can be performed, said chamber having a proximate zone and a distal zone and means for controlling overall rate of liquid flow through said chamber, said means for controlling comprising said non-impregnated region of said second layer which non-impregnated region is in liquid communication with said chamber and wherein a portion of the non-impregnated region is positioned within the distal zone of said chamber.

2. The device of claim 1 wherein said liquid absorbent material comprises a cellulosic material.

3. The device of claim 2 wherein said cellulosic material comprises paper.

4. The device of claim 3 wherein said paper comprises filter paper.

5. The device of claim 1 wherein said third layer is hydrophobic.

6. The device of claim 1 wherein said slot is substantially formed within said impregnated, liquid-occlusive region and defines at least approximately parallel walls in said proximate zone thereby defining a first path of approximately constant width and defining walls in said distal zone which are spaced to define a second path of increased width compared to said first path whereby agglutination reactions in said chamber result in the formation of one or more bands of agglutinated particles in said distal zone of said chamber which bands are visibly observable through said window of said third layer.

7. The device of claim 6 wherein said slot defines walls in said distal zone which are spaced to provide said second path such that agglutination reactions in said chamber result in said bands of agglutinated particles being approximately semicircular in configuration.

8. The device of claim 6 wherein said slot defines walls in said distal zone which are spaced to provide a decreased flow rate per unit area of liquid along said second path.

9. The device of claim 6 wherein said slot defines walls in said distal zone which are spaced to provide said second path with a flared configuration relative to said first path.

10. The device of claim 9 wherein said flared configuration is approximately deltoid in shape.

11. The device of claim 9 wherein said flared configuration is approximately semicircular in shape.

12. The device of claim 6 wherein said slot defines walls in said distal zone which are spaced to provide said second path with an approximately rectangular shape.

13. The device of claim 1 in which said third layer contains a well-defining slot and said second layer contains a corresponding second well-defining slot of the same size and configuration as said well-defining slot in said third layer and positioned directly below said well-defining slot in said third layer, wherein said second well-defining slot in conjunction with said well-defining slot in said third layer and said first layer define a well for receiving liquid, said well being in liquid communication with said proximate zone of said chamber.

14. A device for performing simultaneously a plurality of agglutination reactions comprising: in adherent relationship, a first hydrophilic layer, a second layer parallel to and overlying said first layer, and a third layer parallel to and overlying said second layer and having windows for observing agglutinated particles, said second layer interposed between and in adherent relationship to said first and third layers, said second layer comprising a liquid-absorbent material selectively impregnated with a substance to form an impregnated region and a plurality of non-impregnated regions wherein said non-impregnated regions are liquid-absorbent and said impregnated region is liquid-occlusive, said second layer including means defining a plurality of slots in radial spatial relationship to each other in said impregnated region and defining channels for directing liquid conducted by capillary action through chambers defined by said slots in conjunction with said first and third layers and within which chambers agglutination reactions can be performed simultaneously, each of said chambers having a proximate zone and a distal zone and means for controlling overall rate of liquid flow through said chamber, said means for controlling comprising a non-impregnated region of said second layer which non-impregnated region is in liquid communication with said chamber and wherein a portion of the non-impregnated impregnated region is positioned within the distal zone of said chamber.

15. The device of claim 14 in which said third layer has a well-defining slot and said second layer has a corresponding second well-defining slot of the same size and configuration as said well-defining slot in said third layer and positioned in said impregnated region directly below said well-defining slot in said third layer, wherein said second well-defining slot in conjunction with said well-defining slot in said third layer and said first layer define a well for receiving liquid, said well being in liquid communication with said proximate zone of each of said chambers.

16. The device of claim 14 wherein said third layer is hydrophobic.

17. An improved device for performing agglutination reactions having at least one chamber having a proximate zone and a distal zone in which chamber agglutination reactions can be performed, the improvement comprising utilization in said device of means for controlling overall rate of liquid flow through said chamber, said means for controlling comprising a layer of liquid-absorbent material selectively impregnated through a thickness thereof with a substance to form an impregnated region and a non-impregnated region wherein said non-impregnated region is liquid-absorbent and said impregnated region is liquid-occlusive and wherein a portion of said non-impregnated region is positioned within said distal zone of said chamber so that said non-impregnated region is in liquid communication with said distal zone of said chamber.

18. The improvement device of claim 17 having a plurality of said chambers and including fluid flow control means comprising said layer of liquid-absorbent material selectively impregnated through a thickness thereof with a substance to form a plurality of impregnated regions and non-impregnated regions, wherein said impregnated regions are liquid-occlusive and said non-impregnated regions are liquid-absorbent and at least one of said non-impregnated regions is in liquid communication and positioned within the distal zone of at least one of said chambers.

19. The improved device of claim 18 wherein said plurality of non-impregnated regions are separated by impregnated regions.

20. The improved device of claim 17 wherein said liquid absorbent material comprises paper.

* * * * *

UNITED STATES PATENT AND TRADEMARK OFFICE
CERTIFICATE OF CORRECTION

PATENT NO. : 5,209,904
DATED : May 11, 1993
INVENTOR(S) : K.J. Forney et al.

It is certified that error appears in the above-identified patent and that said Letters Patent is hereby corrected as shown below:

Column 12, line 23, after "non-impregnated" delete --impregnated--.

Signed and Sealed this

First Day of March, 1994

Attest:

BRUCE LEHMAN

Attesting Officer        Commissioner of Patents and Trademarks